US00PP36660P2

(12) United States Plant Patent
Sproul

(10) Patent No.: US PP36,660 P2
(45) Date of Patent: May 13, 2025

(54) FLORIBUNDA ROSE PLANT NAMED 'Spropuff'

(50) Latin Name: *Rosa hybrida*
Varietal Denomination: Spropuff

(71) Applicant: The Conard Pyle Company, West Grove, PA (US)

(72) Inventor: James Sproul, Bakersfield, CA (US)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/522,617

(22) Filed: Nov. 29, 2023

(51) Int. Cl.
*A01H 5/02* (2018.01)
*A01H 6/74* (2018.01)

(52) U.S. Cl.
USPC ..... Plt./148

(58) Field of Classification Search
USPC ..... Plt./141, 148
See application file for complete search history.

(56) References Cited

U.S. PATENT DOCUMENTS

| | | | |
|---|---|---|---|
| PP12,579 | P2 | 4/2002 | Meilland |
| PP18,473 | P2 | 2/2008 | Carruth |
| PP28,993 | P2 | 2/2018 | Radler |
| PP32,663 | P2 | 12/2020 | Sproul |

OTHER PUBLICATIONS https://helpmefind.com/rose/l.php?l=2.89518.1 (retrieved online Oct. 1, 2024) (Year: 2024).*

Help Me Find Roses, Clematis and Peonies and everything gardening related, Conard-Pyle (Star Roses); https://helpmefind.com/gardening/l.php?l=18.3057 (downloaded on Jan. 27, 2025).

Star Roses and Plants—Our History, https://starrosesandplants.com/industry/about-us/history/ (downloaded on Jan. 27, 2025).

* cited by examiner

*Primary Examiner* — Susan McCormick Ewoldt
*Assistant Examiner* — Zachariah Allan Kay
(74) *Attorney, Agent, or Firm* — Panitch Schwarze Belisario & Nadel LLP; Stephany G. Small; Travis W. Bliss

(57) ABSTRACT

A new and distinct variety of floribunda rose plant, referred to by its cultivar name, 'Spropuff', is described. The new variety forms in abundance on a substantially continuous basis medium pink colored blossoms. The growth habit is very bushy and upright to rounded. Glossy foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'Spropuff'.

STATEMENT REGARDING PRIOR DISCLOSURES BY THE INVENTOR

The first offer for sale of the new variety was December 2022. The first offer for sale of the new variety was by the inventor or another who obtained the new variety directly or indirectly from the inventor. The first offer for sale was by Star® Roses and Plants. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of floribunda rose plant of the present invention was created by controlled breeding in April 2016, in Bakersfield, California by artificial pollination wherein two parents were crossed which previously had been studied in the hope that they would contribute the desired characteristics. The female parent (i.e., the seed parent) of the new variety was an unnamed breeder seedling (not patented), which was the product of the cross of a different unnamed seedling and 'WEKvossutono' (U.S. Plant Pat. No. 18,473; Julia Child™), wherein the different unnamed seedling was a product of the cross of 'Meimonblan' (U.S. Plant Pat. No. 12,579; Marmalade Skies™) and 'Baby Love' (not patented). The male parent (i.e., the pollen parent) of the new variety was the 'Sprogreatpink' variety (U.S. Plant Pat. No. 32,663).

The parentage of the new variety can be summarized as follows:

('Meimonblan' x 'Baby Love'] x 'WEKvossutono')
x 'Sprogreatpink'

The seeds resulting from the above pollination were sown and small plants were obtained which were physically and biologically different from each other. Selective study resulted in the identification of a single plant of the new variety.

The new variety has been found to undergo asexual propagation at Wasco, California and Cochranville, Pennsylvania by a number of routes such as vegetative cuttings. Asexual propagation techniques in Wasco, California and Cochranville, Pennsylvania such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of floribunda rose plant of the present invention possesses the following combination of characteristics:

(a) forms medium pink colored blossoms, (b) exhibits a very bushy and upright to rounded growth habit, and (c) provides glossy, dark green colored foliage.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the unnamed breeding seedling female parent (i.e., the seed parent) produces flowers with less petals compared to the medium pink colored flowers of the new variety. Additionally, the new variety produces a higher petal count and a more upright growth habit compared to the 'Sprogreatpink' variety (i.e., the pollen parent). Moreover, the new variety can be readily distinguished from non-parental related similar varieties. For example, 'Radshining' (U.S. Plant Pat. No. 28,993) displays less petals and deep pink colored flowers compared to the medium pink colored flowers of the new variety.

The new variety has been named the 'Spropuff' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was photographed in April 2022, and was approximately two years of age and was grown outdoors in a field on its own roots in Arroyo Grande, California.

Drawing illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on two-years-old specimens of the new variety, observed during February, while growing in a 3-gallon container on its own roots in a greenhouse in Cochranville, Pennsylvania.

Botanical classification: *Rosa hybrida* cultivar 'Spropuff'.

Commercial classification: Floribunda Rose.

Plant:

*Habit*.—Very bushy and upright to rounded.

*Height*.—Approximately 52.0 cm on average from the top of the soil plane in 3-gallon pot.

*Width*.—Approximately 48.0 cm on average.

Branches:

*Stems*.—Color: Young stems: Green Group 143A. Old wood: Green Group 137A. Length: Main stems: Approximately 30.0 cm on average. Secondary stems: Approximately 18.0 cm on average. Diameter: Main stems: Approximately 7.0 mm on average. Secondary stems: Approximately 3.0 mm on average. Texture: Smooth unless interrupted by prickles.

*Prickles*.—Amount: Few, 1 to 2 per internode. Young Prickles: Color: Yellow-Green Group 152A. Size: Length: Approximately 6.0 mm on average. Width: Approximately 4.0 mm at point of attachment. Old Prickles: Color: Greyed-Orange Group 177C. Size: Length: Approximately 6.0 mm on average. Width: Approximately 3.0 mm at point of attachment.

Foliage:

*Color* (*young foliage*).—Upper Surface: Yellow-Green Group 144A with indistinguishable venation. Under Surface: Yellow-Green Group 144C with indistinguishable venation.

*Color* (*old foliage*).—Upper Surface: Green Group NN137A with indistinguishable venation. Under Surface: Yellow-Green Group 147B with venation of Greyed-Orange Group 172A.

*Leaf margin*.—Serrate, undulation is moderate.

*Leaflets*.—Number: 3, 5, and 7. Shape: Ovate. Apex: Acute to acuminate. Base: Cuneate Arrangement: Alternate. Texture: Upper Surface: Smooth. Under Surface: Smooth. Venation pattern: Reticulate. Glossiness of upper side of leaf: Glossy. Size: Terminal Leaflet Length: Approximately 6.3 cm on average. Width: Approximately 4.0 cm on average. Lower Leaflets Length: Approximately 3.5 cm on average. Width: Approximately 2.5 cm on average. 5-Leaflet leaf Length: Approximately 12.0 cm on average. Width: Approximately 10.0 cm on average.

*Petiole*.—Length: Approximately 3.2 cm on average. Diameter: Approximately 1.0 mm on average. Texture: Upper surface: Smooth. Under surface: Smooth. Color: Upper surface: Green Group 137A. Under surface: Yellow-Green Group 147B.

*Rachis*.—Length: Approximately 9.0 cm on average. Diameter: Approximately 1.0 mm on average. Color: Upper surface: Green Group 137A. Under surface: Yellow-Green Group 147B.

*Stipules*.—Length: Approximately 1.2 cm on average. Width: Approximately 5.0 mm on average. Margin: Entire to erose. Color: Upper surface: Green Group 143B. Under surface: Green Group 143C.

Inflorescence:

*Number of flowers*.—About 22 blooms on average on a plant at once.

*Number of blossoms per stem*.—Typically, two to four blooms per stem on average.

*Peduncle*.—Color: Yellow-Green Group 144A. Diameter: Approximately 3.0 mm on average. Length: Approximately 4.0 cm on average. Surface Texture: Smooth with a few small prickles.

*Sepals*.—Number: 5. Upper surface color and texture: Covered in short pubescence, Yellow-Green Group 144A. Under surface color and texture: Puberulent, Yellow-Green Group 148B. Size: Length: Approximately 1.8 cm on average. Width: Approximately 9.0 mm on average. Margin: Entire with extensions on two or three sepals measuring approximately 5.0 mm in length and approximately 1.0 mm in width. Shape: Lanceolate. Apex: Acute to aristate. Base: Truncate as it joins the receptacle.

*Buds*.—Shape: Ovoid. Size: Length: Approximately 1.5 cm on average. Width: Approximately 1.3 cm on average. Color (when opening): Red-Purple Group 58B.

*Flower*.—Form: Double, cuplike. Diameter: Approximately 7.6 cm on average. Height: Approximately 2.7 cm on average. Profile: Flat to slightly concave as it opens. Duration: On the plant approximately 10 to 12 days. Fragrance: Moderate sweet scent.

*Petal*.—Color when first and fully open: Upper Surface: Red-Purple Group 61C with a medium sized basal spot of Yellow Group 6A. Under Surface: Red-Purple Group 63B with a medium sized basal spot of Yellow Group 6C. Color at end of blooming: Upper Surface: Red Group 54B with a medium sized basal spot of Yellow Group 2D. Under Surface: Largely Red Group 54C transitioning to Red Group 56A towards petal margin with no distinct basal spot. Petal Texture of upper and lower surfaces: Smooth. Petal Margin: Entire with a moderate undulation. Petals reflex one by one: Yes. Petal number: 73 on average. Petal drop: Good. Length: Approximately 3.5 cm on average. Width: Approximately 3.4 cm on average. Overall Shape: Broadly obovate. Apex Shape: Rounded to slightly cuspidate. Base Shape: Cuneate.

*Petaloids*.—Number: On average, 5 per flower. Color: Red-Purple Group 61C transitioning to Yellow Group 6A towards the point of attachment. Length: Approximately 1.5 cm on average. Width: Approximately 5.0 mm on average. Texture: Smooth. Margins: Entire. Shape: Obcordate. Apex: Obcordate. Base: Cuneate.

*Stamen*.—Number: Approximately 120. Anthers — Number: Approximately 120. Color: Yellow-Orange Group 20A. Shape: Oval. Length: Approximately 3.0 mm on average. Filaments — Length: Approximately 2.0 mm on average. Color: Yellow Group 12A.

*Pistils*.—Arrangement: Separate and free. Number: Approximately 96. Style: Color: Yellow Group 9C. Length: Approximately 4.0 mm on average. Stigma: Color: Yellow Group 9B. Diameter: Approximately 1.0 mm on average. Shape: Fan shaped.

*Receptacle*.—Diameter: Approximately 1.0 cm on average. Depth: Approximately 6.0 mm on average. Shape: Urn shaped. Color: Yellow-Green Group 144A. Surface Texture: Smooth.

*Pollen*.—None observed. Amount: Sparse. Color: Yellow-Orange Group 20A.

*Hips/seed formation*.—None observed.

Development:

*Vegetation*.—Dark green.

*Blossoming*.—Abundant and substantially continuous from spring through frost.

*Hardiness*.—Hardy to USDA Zone 5, further hardiness testing is in process.

*Resistance to diseases*.—Excellent resistance for Powdery Mildew (*Sphaerotheca pannosa*) and rust (*Phragmidium* sp.).

The new 'Spropuff' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of floribunda rose plant named 'Spropuff' characterized by the following combination of characteristics:

(a) forms medium pink colored blossoms, (b) exhibits a very bushy and upright to rounded growth habit, and (c) provides glossy, dark green colored foliage;

substantially as herein shown and described.

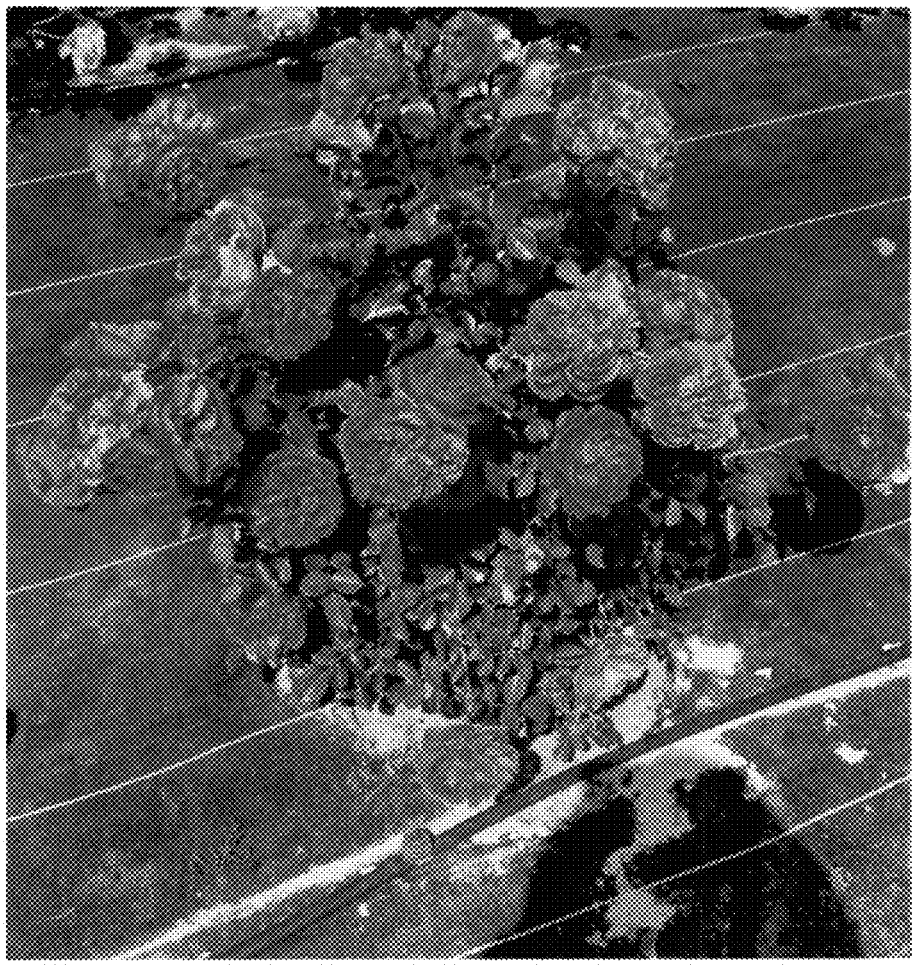

* * * * *